(12) United States Patent
Ogden et al.

(10) Patent No.: US 9,382,577 B2
(45) Date of Patent: Jul. 5, 2016

(54) BIOLOGICAL SAMPLE COLLECTION

(71) Applicant: GE HEALTHCARE UK LIMITED, Little Chalfont (GB)

(72) Inventors: Samantha Jane Ogden, Cardiff (GB); Leonard J. Goren, Piscataway, NJ (US)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 0 days.

(21) Appl. No.: 14/374,270

(22) PCT Filed: Jan. 31, 2013

(86) PCT No.: PCT/EP2013/051950
§ 371 (c)(1),
(2) Date: Jul. 24, 2014

(87) PCT Pub. No.: WO2013/113842
PCT Pub. Date: Aug. 8, 2013

(65) Prior Publication Data
US 2014/0370513 A1 Dec. 18, 2014

(30) Foreign Application Priority Data
Jan. 31, 2012 (GB) .................................. 1201645.7

(51) Int. Cl.
*A61B 10/00* (2006.01)
*C12Q 1/68* (2006.01)
*G01N 1/02* (2006.01)
*G01N 1/00* (2006.01)

(52) U.S. Cl.
CPC ............... *C12Q 1/6806* (2013.01); *G01N 1/02* (2013.01); *G01N 2001/007* (2013.01); *G01N 2001/028* (2013.01)

(58) Field of Classification Search
CPC .......................................................... A61B 5/00
USPC .................................. 600/562, 569, 570, 572
See application file for complete search history.

(56) References Cited

U.S. PATENT DOCUMENTS 3,343,540 A * 9/1967 Siegel ............................. 604/1
3,431,909 A * 3/1969 Krusko ........................... 604/15
(Continued)

FOREIGN PATENT DOCUMENTS

WO     2005/023426 A2   3/2005
WO     WO 2007/106552   9/2007

OTHER PUBLICATIONS

Chinese Office Action for CN Application No. 201380007390.9 mailed Oct. 10, 2015 (17 pages).
(Continued)

*Primary Examiner* — Rene Towa
*Assistant Examiner* — May Abouelela
(74) *Attorney, Agent, or Firm* — Sutherland Asbill & Brennan LLP

(57) ABSTRACT

Disclosed is a device (10) for collecting a biological sample, the device comprising an elongate handle (40) extending generally along a handle axis, and a sample collecting head (20) removably supported or supportable on the handle, the head being formed from a porous folded planar or sheet material, optionally including a plurality of arms (22-28 FIG. 2) each extending away from the handle axis in a different direction. An ejection handle is provided. Disclosed also is an efficient method for extracting DNA information from the device.

11 Claims, 5 Drawing Sheets

(56) References Cited

U.S. PATENT DOCUMENTS

| | | | | |
|---|---|---|---|---|
| 3,610,243 | A * | 10/1971 | Jones, Sr. | 604/375 |
| 3,626,470 | A * | 12/1971 | Antonides et al. | 600/572 |
| 3,628,533 | A * | 12/1971 | Loyer | 604/14 |
| 3,800,781 | A * | 4/1974 | Zalucki | 600/562 |
| 3,838,681 | A * | 10/1974 | Dalton | 600/570 |
| 4,175,008 | A * | 11/1979 | White | 600/572 |
| 4,448,205 | A * | 5/1984 | Stenkvist | 600/562 |
| 5,137,030 | A * | 8/1992 | Darougar | 600/570 |
| 5,278,075 | A * | 1/1994 | Stone | 436/73 |
| 5,477,863 | A | 12/1995 | Grant | |
| 5,746,710 | A * | 5/1998 | Nielsen et al. | 604/14 |
| 5,782,793 | A * | 7/1998 | Nielsen et al. | 604/14 |
| 5,792,096 | A * | 8/1998 | Rentmeester et al. | 604/14 |
| 6,036,658 | A * | 3/2000 | Leet et al. | 600/569 |
| 6,059,735 | A * | 5/2000 | Sgro | 600/569 |
| 6,206,867 | B1 * | 3/2001 | Osborn et al. | 604/385.18 |
| 6,258,044 | B1 * | 7/2001 | Lonky et al. | 600/569 |
| 6,612,996 | B2 * | 9/2003 | Williams | 600/569 |
| 6,840,911 | B2 * | 1/2005 | Sangha | 600/582 |
| 6,890,324 | B1 * | 5/2005 | Jackson et al. | 604/385.17 |
| D516,718 | S * | 3/2006 | Weber et al. | D24/141 |
| 7,098,040 | B2 * | 8/2006 | Kaylor et al. | 436/514 |
| 7,226,436 | B2 * | 6/2007 | Gorham et al. | 604/385.17 |
| D572,362 | S * | 7/2008 | Edgett et al. | D24/141 |
| 7,767,448 | B2 * | 8/2010 | Yong | 435/309.1 |
| 8,323,211 | B2 * | 12/2012 | Larkin | 600/569 |
| 8,475,394 | B1 * | 7/2013 | Stivers | 600/572 |
| 8,630,016 | B2 | 1/2014 | Swenson et al. | |
| 8,696,595 | B2 * | 4/2014 | Sangha | 600/572 |
| 2002/0111562 | A1 * | 8/2002 | Richards | 600/562 |
| 2003/0113906 | A1 * | 6/2003 | Sangha et al. | 435/287.2 |
| 2005/0136479 | A1 * | 6/2005 | Lyng et al. | 435/7.1 |
| 2005/0256486 | A1 * | 11/2005 | Carasso et al. | 604/385.18 |
| 2005/0277846 | A1 * | 12/2005 | Chou | 600/569 |
| 2009/0043224 | A1 * | 2/2009 | Lundkvist et al. | 600/562 |
| 2009/0048439 | A1 * | 2/2009 | Weisburg et al. | 536/25.41 |
| 2009/0098559 | A1 | 4/2009 | Caragine et al. | |
| 2009/0260205 | A1 * | 10/2009 | Binner et al. | 28/118 |
| 2010/0069791 | A1 * | 3/2010 | Ernster | 600/569 |
| 2010/0121219 | A1 * | 5/2010 | McCabe et al. | 600/570 |
| 2010/0249649 | A1 * | 9/2010 | Larkin | 600/569 |
| 2010/0307266 | A1 | 12/2010 | Ward | |
| 2011/0021950 | A1 * | 1/2011 | Daniels | 600/569 |
| 2011/0172557 | A1 | 7/2011 | Lonky et al. | |
| 2013/0172778 | A1 * | 7/2013 | Teschendorf | 600/569 |
| 2013/0338533 | A1 * | 12/2013 | Olsen | 600/569 |
| 2014/0024069 | A1 * | 1/2014 | Figueredo | 435/29 |

OTHER PUBLICATIONS

Chinese Search Report for CN Application No. 201380007390.9 mailed Oct. 10, 2015 (5 pages).

* cited by examiner

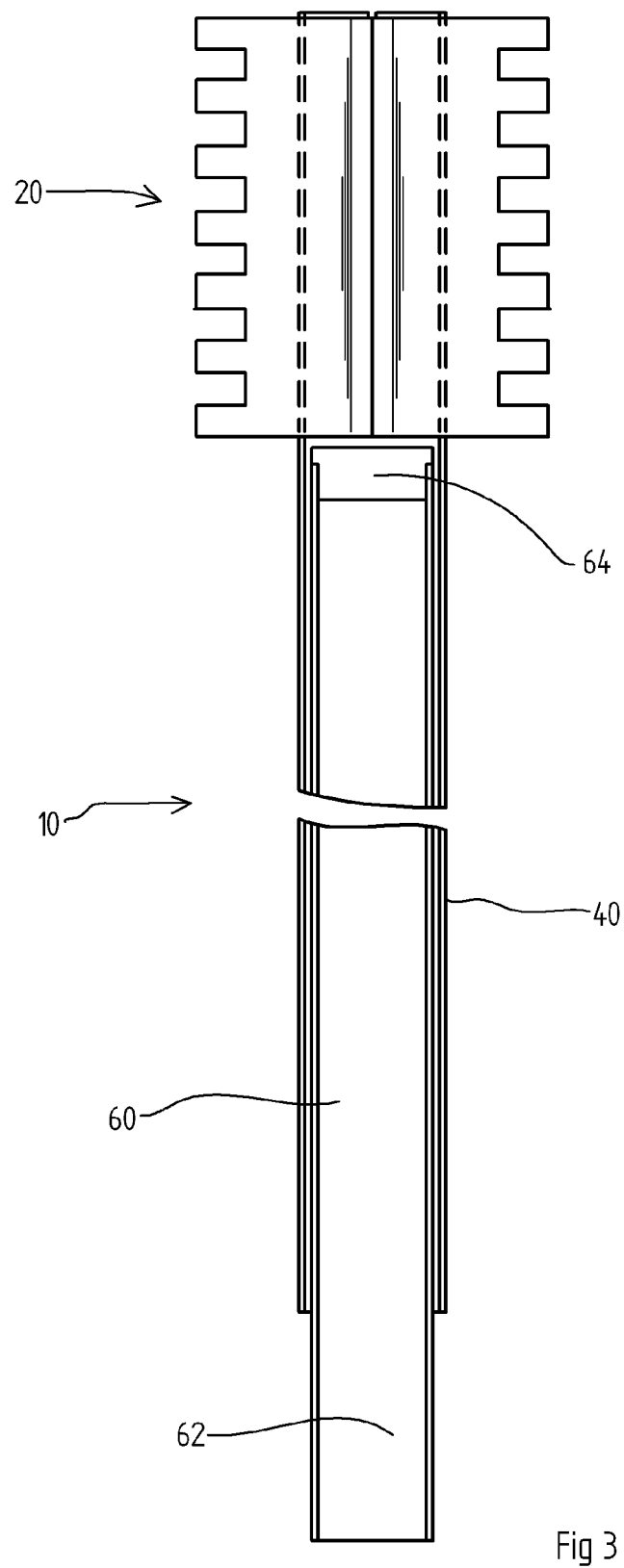

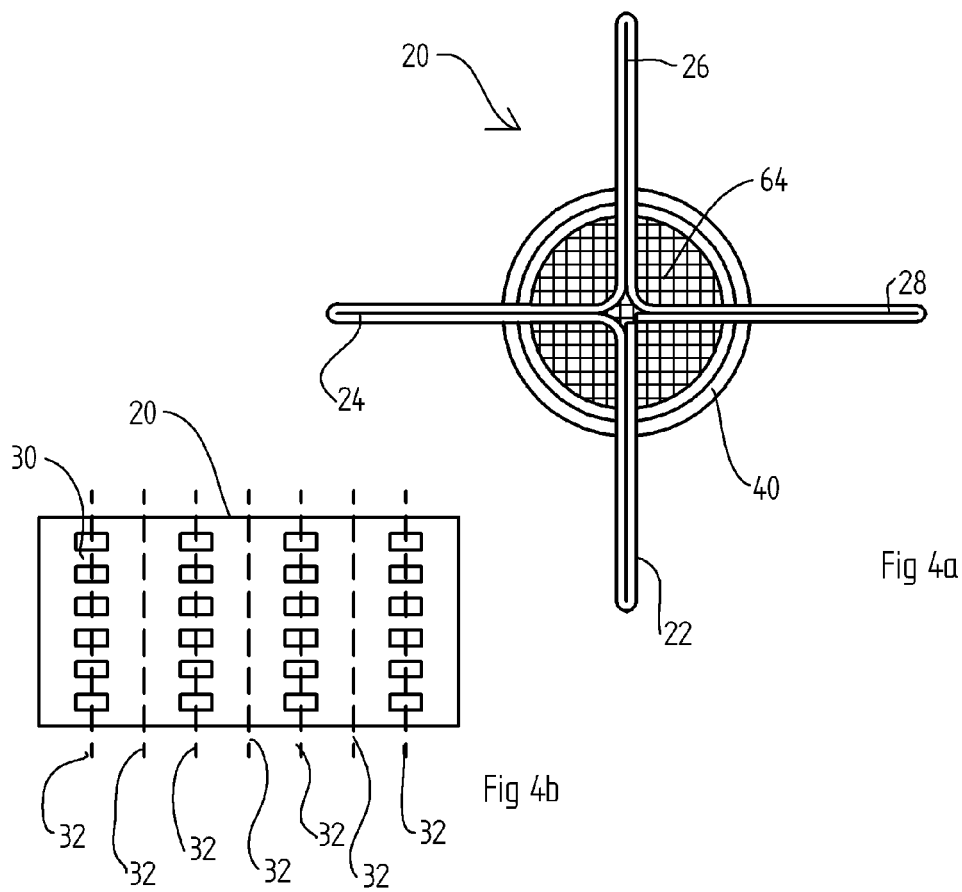
Fig 4a
Fig 4b
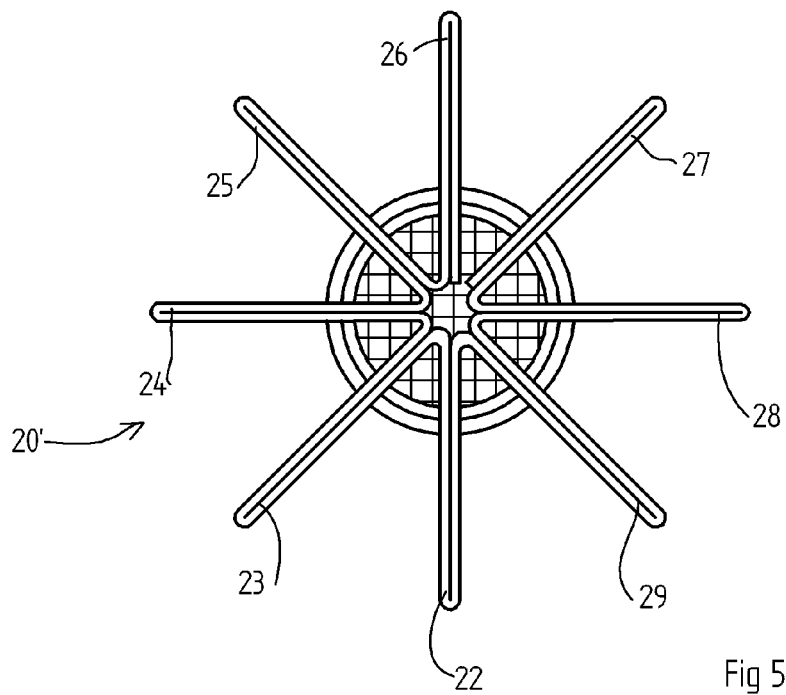
Fig 5

BIOLOGICAL SAMPLE COLLECTION

CROSS-REFERENCE TO RELATED APPLICTIONS

This application is a filing under 35 U.S.C. 371 of international application number PCT/EP2013/051950, filed Jan. 31, 2013, published on Aug. 8, 2012 as WO 2013/113842, which claims priority to application number 1201645.7 filed in Great Britain on Jan. 31, 2012.

The present invention relates principally to a swab-like device for collecting biological samples, and a method for obtaining nucleic acid information from such a device when the device holds a biological sample.

It is desirable to collect biological samples for various reasons, such as crime scene investigations, medical analysis, genetic recording and the like. Traditionally, a sterile swab, having the trade name Omni-Swab, has been used for this purpose with reasonable success. The process involves contacting an area where a desired biological sample it located, in order to transfer at least some of the sample from the area, to the swab. However, in some cases it is difficult to make contact with the whole of the area where the area has inaccessible features. Therefore, the inventors have realised that the design of these swabs can be improved to increase the chances of transferring biological material from the area of interest to the swab. For example, during crime scene investigations, it is often necessary to rub the whole of an item to maximise the chances of obtaining a sample. However it is often very difficult to access small orifices, narrow recesses and the like with a conventional swab.

It is known to use a thin substrate such as filter type paper as a sample collector, because it is relatively easy to remove the biological sample from the paper once it is collected. However, the thin paper has been found to be weak in use, particularly where paper is used in an attempt to collect a sample from a small orifice, a narrow recess or the like. Further, once collected on a filter paper substrate, the known process for obtaining DNA or RNA information from the paper is time consuming, and not always successful. The inventor has realised that changes in the chemistry of the collecting portion of the swab can improve the recovery rate of the biological sample, and the speed of analysis of the sample.

Embodiments of the invention address the deficiencies mentioned above.

According to a first aspect the invention provides a device for collecting a biological sample, the device comprising an elongate handle extending generally along a handle axis, and a sample collecting head removably supported or supportable on the handle, the head being formed from a porous substrate formed from folded generally planar or sheet material, for example a paper material.

Thus the head can be used to collect a biological sample more efficiently than a conventional swab.

In an embodiment, said substrate is for example a paper material, and is preferably folded to form arms extending away from said axis.

In an embodiment, the handle is a hollow tube providing a tube wall having an outer handle surface.

In an embodiment, the arms each pass through a respective corresponding slot extending through said wall, said slots running parallel to the axis.

In an embodiment there are 2 to 12 slots in an array, preferably 2, 3, 4, 5, 6, 7 or 8 slots, and more preferably 2, 3, 4 or 6 slots.

In an embodiment, the handle includes a slidable ejector pin held in use within the tube, having a first end which extends beyond the tube at one end of the tube, the other end of said ejector pin being engageable with a portion of the head for ejecting the head from the slots in the tube.

In an embodiment, the substrate or paper is a matrix containing a conjugate base of thiocyanic acid, for example Guanidinuim Thiocyanate and optionally an indicating dye, for example Chlorophenol red.

According to a second aspect the invention provides a method for collecting a biological sample, including the following steps, in any suitable order:
a) providing a sample collection device according to the first or second aspect;
b) dampening the head of said collection device with sterile liquid;
c) attempting to collect a biological sample on the head;
d) allowing the head to dry.

According to a third aspect the invention provides a method of recovering nucleic acid information from a biological sample collected on a sample collection device, the method comprising the following steps in any suitable order:
e) following steps a) to d) above;
f) removing the head of the device;
g) introducing into a vessel the head, or a portion thereof, together with a rinsing liquid;
h) agitating the vessel and its contents;
i) removing at least a portion of said rinsing liquid from the vessel and optionally applying centrifugal force to remove further rinse liquid;
j) in a chamber, combining elution liquid and the rinsed head or said portion thereof;
k) heating the contents of said chamber to approximately 95 degrees Celsius for approximately 30 minutes, and optionally further agitating and/or optionally applying further centrifugal force to said chamber contents; and
l) using at least a portion of the elution liquid resulting from step k) in a reaction to amplify nucleic acids therein, for example a polymerase chain reaction (PCR), to thereby obtain said nucleic acid information.

The invention can be put into effect in numerous ways, exemplary embodiments only being described below, with reference to the drawings wherein:

FIG. 3 shows a sectional view of the device shown in FIG. 1; and

FIGS. 4a, 4b, show further views of the device shown in FIG. 1; and

FIGS. 5 and 6 show alternative head arrangements.

Figure 1:
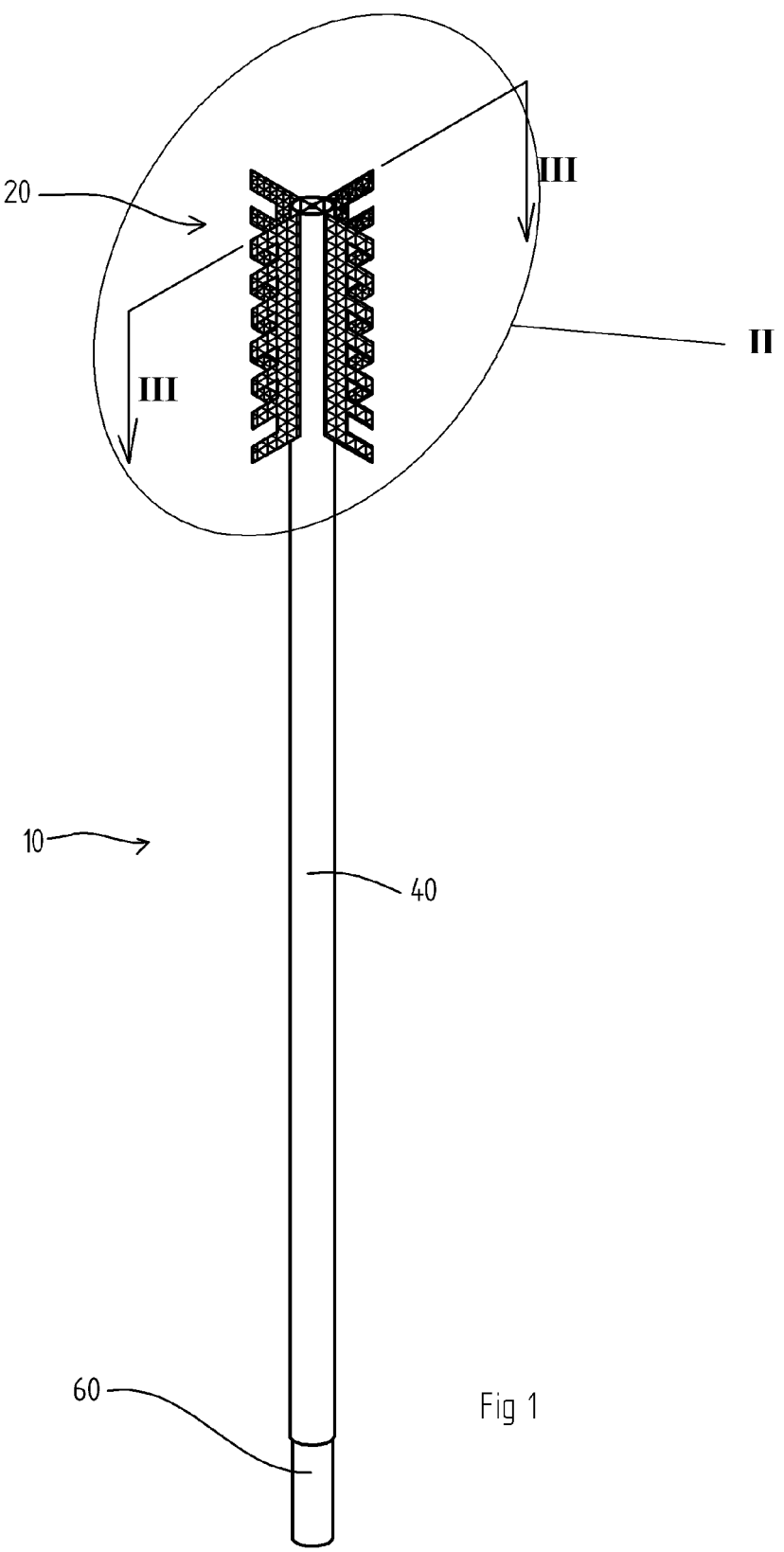
FIG. 1 shows a sample collection device.

FIG. 1 shows a sample collection device 10, comprising a sample collection head 20, a hollow tubular handle 40, and an ejector pin 60. The device is about 150 mm in overall length, with a head about 10 mm across and 20 mm long.

Figure 2:
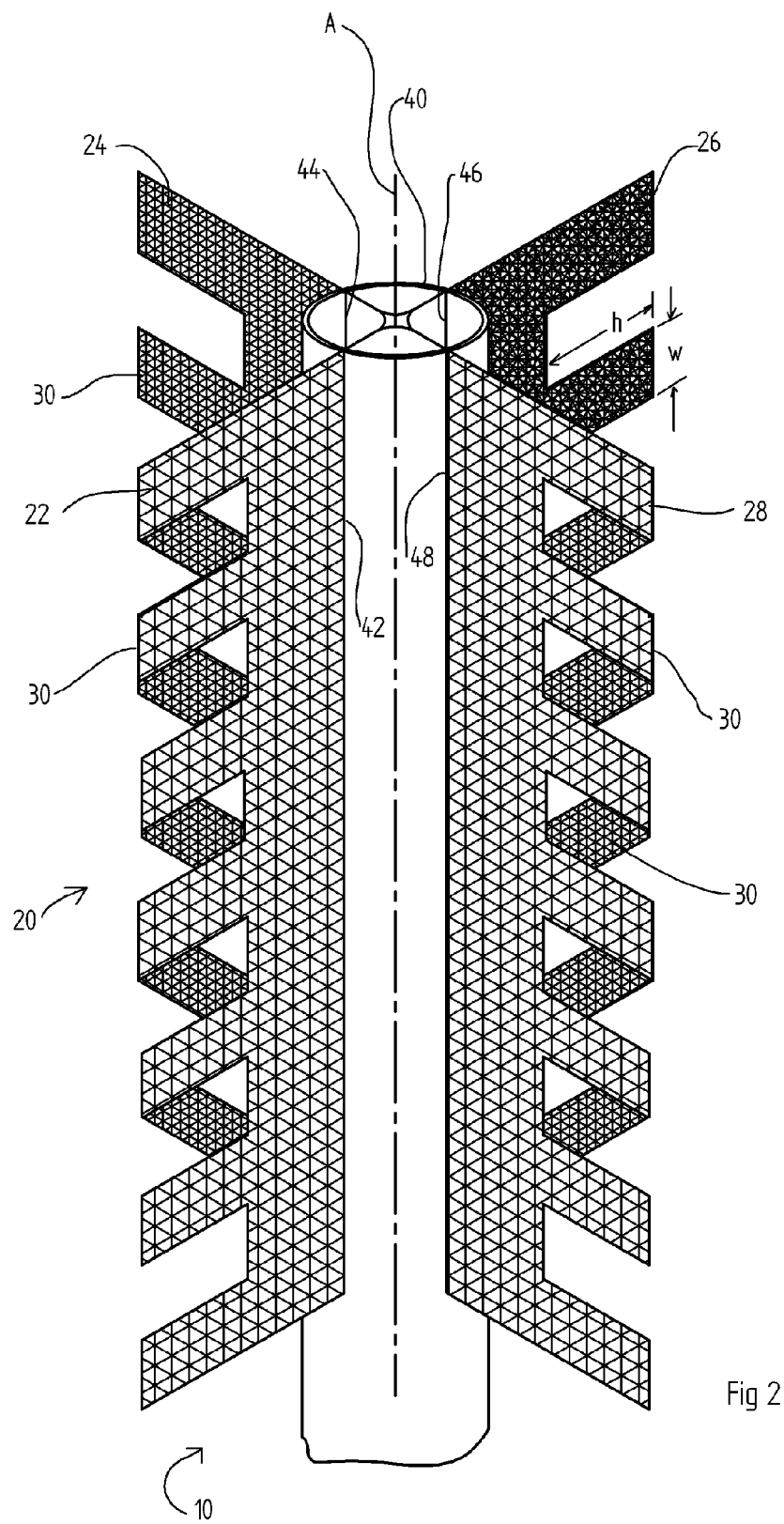
FIG. 2 shows an enlarged view of a head portion of the device shown in FIG. 1.

Referring additional to FIG. 2, which shows an enlarged view of the area II in FIG. 1, the head has four arms 22, 24, 26 and 28 each fitting into a respective slot 42, 44, 46, and 48 formed in the tubular handle 40. The arms 22, 24, 26 are formed from a single sheet of sample collection paper, folded into a cross shape with each leg pushed into a respective slot in a manner which allows for removal of the head from the slots. This means that each arm extends away from the handle axis in a different direction—in this case at 90 degrees to each other. The arms have castellations 30 only one of which is reference for each arm. These castellations provide 'teeth' about 1.6 mm in width (w) and about 2 mm in height (h), which can penetrate into small apertures and the like for more effective collection of potential biological samples.

FIG. 3 shows a sectional view of the device 10, in the plane III-III shown in FIG. 1. In this view the hollow tubular handle 40 is visible, and the ejector pin 60 is shown also. The pin has a portion 62 which extends beyond the lower end of the handle 40. The opposite end of the ejector pin 60 has a plug 64 which can make contact with the head 20. The portion 62 can be pushed by a user so as to force the plug in the direction of arrow E and thereby to force the head 20 off the handle 40.

FIG. 4a shows an enlarged end view of the device 10. In this view the arms 22-28 can be seen folded, such that they are each formed from a double sheet of paper, but only one cut sheet is needed. This folding stiffens the arms so that the user is able to rub the head more firmly against an area of interest. Four arms are shown in this embodiment, equispaced around the axis of the handle, but other numbers of arms are possible.

FIG. 4b shows a developed (unfolded) view of the head 20 of FIG. 4a, which can be punched from a paper material, then folded along dotted fold lines 32 to form the head shown in FIGS. 2 and 4. The head is pushed into the slots shown in FIG. 2 during assembly.

FIG. 5 shows a head arrangement 20' which is similar to that shown in FIG. 4, but in FIG. 5, eight arms 22,23,24,25,26,27,28,29 are arranged around the handle axis. A punched and folded construction (not shown) similar to that shown in FIG. 4a can be produced to form the arms shown in FIG. 5.

Figure 6:
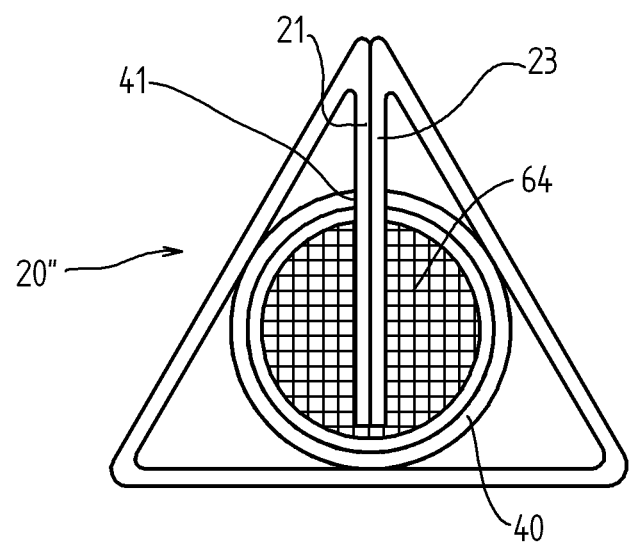

FIG. 6 shows a further head 20". In this embodiment the paper material is folded into a triangular shape with a pair of inwardly directed opposed legs 21 and 23 placed together to form a support, stiffened portion which can sit within a single slot 41 in the handle 40, and can be used to eject the head once it has been used. It will be appreciated that the pair of legs 21 and 23 could be folded inwardly at any point of the triangular periphery shown. Further, the triangular shape could be replaced by any polygonal shape or an irregular shape, with generally comparable utility. So square and hexagonal shapes will suffice, although the greater the number of sides, the more difficult it becomes to access narrow features, for example during forensic examination.

In use the device is supplied assembled as shown in FIG. 1, in a sterile packaging (not shown), and is removed therefrom immediately prior to use. The head 20 is dampened with sterile water, and the device can be manipulated so that the castellations 30 of the head collect biological samples, for example potential DNA samples, or the like, at a crime scene. The head 20 need not be touched directly by the user. The head can be ejected from the handle into a tamper evident sterile bag once dried.

The recovery of nucleic acid information (for example from DNA), from swabs is known, but the speed and success rate of this operation has been found to be enhanced by the use of the following techniques:

The paper has been treated with Guanidinuim Thiocyanate, by dipping a web of the paper into a solution of Guanidinuim Thiocyanate during manufacture of the paper and then drying the paper web. This treatment has the result that certain steps in known nucleic acid information recovery techniques can be circumvented or shortened in time.

The head of the sample collection device, once brought into contact with the area of interest, and then dried, is treated according to the following steps:
1) Remove device from taper evident bag;
2) Eject head from device into a vessel;
3) Rinse head in 1000 µl of water, pulse vortex (agitate) 3 times for 5 seconds
4) Remove excess water and centrifuge head for 5 seconds;
5) Remove excess water using a pipette or the like;
6) Add 200-500 µl of sterile water to the vessel, heat at 95° C. for 30 minutes; pulse vortex (agitate) 60 times;
7) Further centrifuge vessel for 5 seconds
8) Use 5 to 10 µl of the sterile water (now containing any DNA from the head) in a now PCR reaction.

This process reduces the number of steps needed to prepare a sample for DNA assay, and so reduces the overall time of the process.

Whilst embodiments of the invention have been described above, additions, omissions, modifications, and variants will be apparent to the skilled addressee. For example the handle 40 is shown as a circular cylinder, but other shapes, such a square tube could be employed with equal effect. The head is preferably made from paper. The term "paper" as used herein means a fibrous web, a matrix, a sheet, or planar material. Paper comprises fibres, e.g. cellulose or glass fibres, and optionally other components, such as e.g. particulate fillers, wet strength or dry strength additives, retention agents etc. It can also comprise reagents for preservation of sample components, lysis of cells etc. Suitable paper substrates and similar porous sheet substrates are sold commercially under the brand names FTA®, FTA®Elute, FTA®DMPK, and 903® by GE Healthcare UK Ltd for preservation of nucleic acid samples. However, other materials such as an absorbent foamed polymer could be used also. Castellated teeth 30 are described and illustrated, but other shapes of teeth could be used, for example pointed or rounded teeth. Four arms 22-28 are shown in FIG. 4a and eight arms 22-29 are shown in FIG. 5, however any number of arms could be employed. A brush effect could be achieved with a multiplicity of arms. The arms need not be equispaced as illustrated.

The invention claimed is:

1. A forensic device for collecting a biological sample, the device comprising: an elongate handle extending substantially along a handle axis, and a rigid sample collecting head attachable to and detachable from the handle, wherein the head is a porous, substantially planar or sheet material folded to form a plurality of arms, each of the plurality of arms extending away from the handle axis in a different direction, wherein the handle is a hollow tube providing a tube wall having an outer handle surface, wherein each of the plurality of arms passes through a respective corresponding slot extending through the tube wall, wherein the handle includes a slidable ejector pin disposed within the handle, wherein a first end of the ejector pin extends beyond a first end of the handle, and wherein a second end of the ejector pin is arranged to engage a portion of the head.

2. The device of claim 1, wherein the tube wall comprises 2 to 12 slots in an array.

3. The device of claim 1, wherein the head is a matrix containing a conjugate base of thiocyanic acid, and wherein said conjugate base of thiocyanic acid recovers nucleic acid information.

4. A method for collecting a biological sample, including the following steps, in any suitable order: a) providing the sample collection device of claim 1; b) dampening the head of said collection device with sterile liquid; c) collecting a biological sample on the head; and d) allowing the head to dry.

5. The device of claim 1, wherein the head is a paper material.

6. The device of claim 1, wherein each slot extends parallel to the axis.

7. The device of claim 3, wherein the conjugate base of thiocyanic acid is Guanidinium Thiocyanate.

8. The device of claim 3, wherein the matrix contains an indicating dye.

9. The device of claim 8, wherein the indicating dye is Chlorophenol red.

10. The device of claim 1, wherein the tube wall comprises 1, 2, 3, 4, 5, 6, 7, or 8 slots in an array.

11. The device of claim 1, wherein the tube wall comprises 1, 2, 3, 4, 5 or 6 slots in an array.

* * * * *